(12) United States Patent
Tsay et al.

(10) Patent No.: US 10,998,580 B2
(45) Date of Patent: May 4, 2021

(54) ELECTROLYTE FOR RECHARGEABLE LITHIUM BATTERY AND RECHARGEABLE LITHIUM BATTERY

(71) Applicant: SAMSUNG SDI CO., LTD., Yongin-si (KR)

(72) Inventors: Olga Tsay, Yongin-si (KR); Pavel Shatunov, Yongin-si (KR); Hyejin Park, Yongin-si (KR); Myungheui Woo, Yongin-si (KR); Harim Lee, Yongin-si (KR); Jin-Hyeok Lim, Yongin-si (KR); Hyunbong Choi, Yongin-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 108 days.

(21) Appl. No.: 16/369,017

(22) Filed: Mar. 29, 2019

(65) Prior Publication Data

US 2019/0305374 A1 Oct. 3, 2019

(30) Foreign Application Priority Data

Apr. 2, 2018 (KR) .......................... 10-2018-0038141

(51) Int. Cl.
*H01M 10/00* (2006.01)
*H01M 10/0567* (2010.01)
(Continued)

(52) U.S. Cl.
CPC ... *H01M 10/0567* (2013.01); *H01M 10/0525* (2013.01); *H01M 10/0568* (2013.01);
(Continued)

(58) Field of Classification Search
CPC ..... H01M 2300/0025; H01M 10/0569; H01M 10/0567; H01M 10/052; C07D 303/48; C07D 303/34
See application file for complete search history.

(56) References Cited

U.S. PATENT DOCUMENTS

2015/0079483 A1 3/2015 Cresce et al.
2016/0172708 A1 6/2016 Porta Garcia et al.
(Continued)

FOREIGN PATENT DOCUMENTS

JP 2016-531389 A 10/2016
KR 10-0283991 B1 12/2000
KR 10-2016-0145055 A 12/2016

OTHER PUBLICATIONS

R. J. Palmer et al., "Elimination and Addition Reactions. 36.[1a,b] Acceleration of Nucleophilic Eliminative Ring Fission by Bond Strain", J. Am. Chem. Soc., 1980, 102, 7888-7892.
(Continued)

*Primary Examiner* — Cynthia H Kelly
*Assistant Examiner* — Monique M Wills
(74) *Attorney, Agent, or Firm* — Lee IP Law, P.C.

(57) ABSTRACT

An electrolyte for a rechargeable lithium battery and a rechargeable lithium battery including the electrolyte, the electrolyte including a non-aqueous organic solvent; a lithium salt; and an additive, wherein the additive includes a compound represented by Chemical Formula 1:

[Chemical Formula 1]

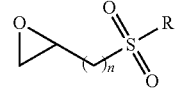

wherein, in Chemical Formula 1, R is a substituted or unsubstituted C1 to C10 alkyl group, a substituted or unsubstituted C1 to C10 alkoxy group, a substituted or unsubstituted C2 to C10 alkenyl group, a substituted or unsubstituted C2 to C10 alkynyl group, a substituted or unsubstituted C3 to C10 cycloalkyl group, a substituted or unsubstituted C3 to C10 cycloalkenyl group, or a substituted or unsubstituted C6 to C20 aryl group, and n is an integer of 1 to 3.

12 Claims, 8 Drawing Sheets

(51) Int. Cl.
*H01M 10/0568* (2010.01)
*H01M 10/0569* (2010.01)
*H01M 10/0525* (2010.01)
C07D 303/34 (2006.01)
C07D 303/48 (2006.01)

(52) U.S. Cl.
CPC ...... *H01M 10/0569* (2013.01); *C07D 303/34* (2013.01); *C07D 303/48* (2013.01); *H01M 2300/0025* (2013.01)

(56) References Cited

U.S. PATENT DOCUMENTS

2016/0172709 A1\* 6/2016 Porta Garcia ..... H01M 10/0567
429/338
2017/0033405 A1 2/2017 Garsuch et al.

OTHER PUBLICATIONS

D. Dana et al., "Design, Synthesis, and Evaluation of 2-(arylsulfonyl)oxiranes as Cell-permeable Covalent Inhibitors of Protein Tyrosine Phosphatases", Chem Biol Drug Des., 2012, 80, 489-499.
Korean Notice of Allowance dated Jul. 15, 2020, of the corresponding Korean Patent Application No. 10-2018-0038141.

\* cited by examiner

ELECTROLYTE FOR RECHARGEABLE LITHIUM BATTERY AND RECHARGEABLE LITHIUM BATTERY

CROSS-REFERENCE TO RELATED APPLICATION

Korean Patent Application No. 10-2018-0038141, filed on Apr. 2, 2018, in the Korean Intellectual Property Office, and entitled: "Electrolyte for Rechargeable Lithium Battery and Rechargeable Lithium Battery," is incorporated by reference herein in its entirety.

BACKGROUND

1. Field

Embodiments relate to an electrolyte for a rechargeable lithium battery and a rechargeable lithium battery including the same.

2. Description of the Related Art

A rechargeable lithium battery may be recharged and has three or more times as high energy density per unit weight as a lead storage battery, nickel-cadmium battery, nickel hydrogen battery, nickel zinc battery, or the like. It may be also charged at a high rate and thus, may be commercially manufactured for a laptop, a cell phone, an electric tool, an electric bike, and the like, and improvement of additional energy density have been considered.

A rechargeable lithium battery may be manufactured by injecting an electrolyte into a battery cell, which includes a positive electrode including a positive active material capable of intercalating/deintercalating lithium ions and a negative electrode including a negative active material capable of intercalating/deintercalating lithium ions.

For example, an electrolyte may include an organic solvent in which a lithium salt is dissolved and may determine stability and performance of a rechargeable lithium battery.

SUMMARY

The embodiments may be realized by providing an electrolyte for a rechargeable lithium battery, the electrolyte including a non-aqueous organic solvent; a lithium salt; and an additive, wherein the additive includes a compound represented by Chemical Formula 1:

[Chemical Formula 1]

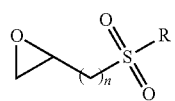

wherein, in Chemical Formula 1, R is a substituted or unsubstituted C1 to C10 alkyl group, a substituted or unsubstituted C1 to C10 alkoxy group, a substituted or unsubstituted C2 to C10 alkenyl group, a substituted or unsubstituted C2 to C10 alkynyl group, a substituted or unsubstituted C3 to C10 cycloalkyl group, a substituted or unsubstituted C3 to C10 cycloalkenyl group, or a substituted or unsubstituted C6 to C20 aryl group, and n is an integer of 1 to 3.

R may be a substituted or unsubstituted C1 to C5 alkyl group or a substituted or unsubstituted C1 to C5 alkoxy group.

The compound represented by Chemical Formula 1 may be included in an amount of 0.1 wt % to 3 wt %, based on a total weight of the electrolyte for a rechargeable lithium battery.

The electrolyte may further include an additional additive, the additional additive including vinylethylene carbonate, fluoroethylene carbonate, propenesultone, propanesultone, lithiumtetrafluoroborate, lithium bis(oxalato)borate, succinonitrile, lithium difluorophosphate, or 2-fluoro biphenyl.

The additional additive may be included in an amount of 0.1 wt % to 10 wt %, based on a total weight of the electrolyte for a rechargeable lithium battery.

The additional additive and the compound represented by Chemical Formula 1 may be included in a weight ratio of 5:1 to 1:5.

The embodiments may be realized by providing a rechargeable lithium battery including a positive electrode; a negative electrode; and the electrolyte according to an embodiment.

R may be a substituted or unsubstituted C1 to C5 alkyl group or a substituted or unsubstituted C1 to C5 alkoxy group.

The compound represented by Chemical Formula 1 may be included in an amount of 0.1 wt % to 3 wt %, based on a total weight of the electrolyte for a rechargeable lithium battery.

The electrolyte may further include an additional additive, the additional additive including vinylethylene carbonate, fluoroethylene carbonate, propenesultone, propanesultone, lithiumtetrafluoroborate, lithium bis(oxalato)borate, succinonitrile, lithium difluorophosphate, or 2-fluoro biphenyl.

The additional additive may be included in an amount of 0.1 wt % to 10 wt %, based on a total weight of the electrolyte for a rechargeable lithium battery.

The additional additive and the compound represented by Chemical Formula 1 may be included in a weight ratio of 5:1 to 1:5.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
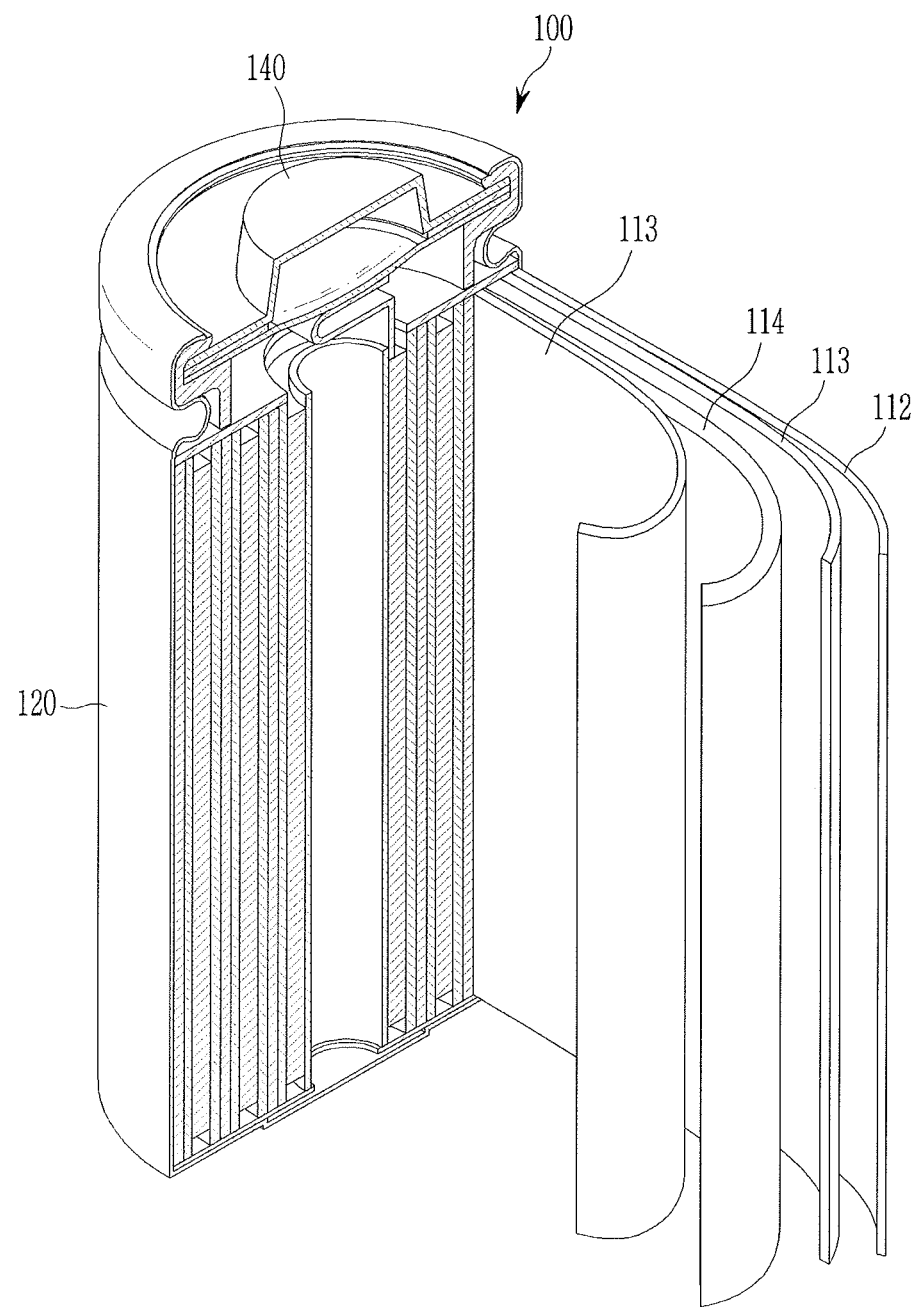
FIG. 1 illustrates a schematic view of a rechargeable lithium battery according to an embodiment of the present disclosure.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

As used herein, when a definition is not otherwise provided, 'substituted' refers to replacement of hydrogen of a compound by a substituent selected from a halogen atom (F, Br, Cl, or I), a hydroxy group, an alkoxy group, a nitro group, a cyano group, an amino group, an azido group, an amidino group, a hydrazino group, a hydrazono group, a carbonyl group, a carbamyl group, a thiol group, an ester group, a carboxyl acid group or a salt thereof, a sulfonic acid group or a salt thereof, a phosphoric acid group or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof.

Hereinafter, an electrolyte for a rechargeable lithium battery according to an embodiment is described.

An electrolyte for a rechargeable lithium battery according to an embodiment may include a non-aqueous organic solvent, a lithium salt, and an additive. In an implementation, the additive may include a compound represented by Chemical Formula 1.

[Chemical Formula 1]

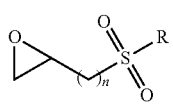

In Chemical Formula 1, R may be or may include, e.g., a substituted or unsubstituted C1 to C10 alkyl group, a substituted or unsubstituted C1 to C10 alkoxy group, a substituted or unsubstituted C2 to C10 alkenyl group, a substituted or unsubstituted C2 to C10 alkynyl group, a substituted or unsubstituted C3 to C10 cycloalkyl group, a substituted or unsubstituted C3 to C10 cycloalkenyl group, or a substituted or unsubstituted C6 to C20 aryl group.

n may be, e.g., an integer of 1 to 3.

When an electrolyte is exposed to a high temperature, $LiPF_6$ that is a kind of lithium salt, may be decomposed into LiF and $PF_5$ in an electrolyte including a small amount of water, and these may react with an organic solvent to consume an organic solvent and may react with the positive electrode to elute metal ions. For example, high-temperature stability and cycle-life characteristics of a lithium battery could be deteriorated.

According to an embodiment, when the additive including the compound represented by Chemical Formula 1 is used, a robust SEI (solid electrolyte interface) film having an excellent ion conductivity may be formed on a surface of a negative electrode. The decomposition of the surface of the negative electrode during a high-temperature cycle operation may be suppressed and an oxidation reaction of the electrolyte may be prevented.

For example, the compound represented by Chemical Formula 1 may be coordinated with a pyrolyzed product of a lithium salt such as $LiPF_6$ or anions dissociated from the lithium salt and thus form a complex, and the complex formation may stabilize the pyrolyzed product of a lithium salt such as $LiPF_6$ or the anions dissociated from the lithium salt. For example, the additive may help suppress an undesired side reaction of the anions with the electrolyte and may help prevent gas generation inside a rechargeable lithium battery and thus greatly reduce a defect rate as well as improve cycle-life characteristics of the rechargeable lithium battery.

In an implementation, the side reaction with the electrolyte may be suppressed, a SEI film and/or protective layer having a low resistance may be formed, and accordingly, battery internal resistance may be reduced.

In an implementation, the compound represented by Chemical Formula 1 and its oxide may participate in an electrochemical reaction with the components of the SEI film to make the film more robust, and may also help improve stability of other components included in the electrolyte due to an oxidative decomposition.

In an implementation, the compound represented by Chemical Formula 1 may be reduction-decomposed on the surface of a negative electrode, may form a reduction decomposition product, and the reduction decomposition product may form a protective layer on a positive electrode. This positive electrode protective layer may help suppress decomposition of the positive electrode by an electrolyte and thus may help prevent a resistance increase of the positive electrode.

In an implementation, a C—C bond of an epoxy ring in the compound represented by Chemical Formula 1 may be broken at a high temperature, a polymerization occurs, and accordingly, the compound represented by Chemical Formula 1 may form the protective layer on the electrode surface, cycle-life performance and high temperature stability of a rechargeable lithium battery may be simultaneously improved by using an electrolyte including the compound represented by Chemical Formula 1.

In an implementation, R may be, e.g., a substituted or unsubstituted C1 to C5 alkyl group, or a substituted or unsubstituted C1 to C5 alkoxy group.

In an implementation, R may be, e.g., a substituted or unsubstituted C1 to C5 alkoxy group.

When R is a substituted or unsubstituted C1 to C5 alkoxy group, storage characteristics at a high temperature may be further improved.

The compound represented by Chemical Formula 1 may be included in an amount of about 0.1 wt % to about 3 wt %, e.g., about 0.1 wt % to about 2 wt % or about 0.1 wt % to about 1 wt %, based on a total weight of the electrolyte for a rechargeable lithium battery.

When the amount of the compound represented by Chemical Formula 1 is in the above ranges, a resistance increase at a high temperature may be prevented, and a rechargeable lithium battery having improved cycle-life characteristics may be realized.

Maintaining the amount of the compound represented by Chemical Formula 1 at about 0.1 wt % or greater may help ensure that deterioration of storage characteristics at a high temperature is prevented. Maintaining the amount of the compound represented by Chemical Formula 1 at about 3 wt % or less may help prevent a deterioration in a cycle-life that could otherwise occur due to an interface resistance increase.

The additive according to an embodiment may further include an additional additive.

In an implementation, the additional additive may include, e.g., vinylethylene carbonate (VEC), fluoroethylene carbonate (FEC), propenesultone (PST), propanesultone (PS), lithiumtetrafluoroborate (LiBF$_4$), lithium bis(oxalato) borate (LiBOB), succinonitrile (SN), lithium difluorophosphate (LiPO$_2$F$_2$), 2-fluoro biphenyl (2-FBP), or a combination thereof.

In an implementation, the additional additive may be included in an amount of about 0.1 wt % to about 10 wt %, e.g., about 0.1 wt % to about 5 wt %, based on the total weight of the electrolyte for a rechargeable lithium battery.

In an implementation, the additional additive and the compound represented by Chemical Formula 1 may be included in a weight ratio of about 5:1 to about 1:5, e.g., about 5:1 to about 1:1 or about 4:1 to about 1:1. In an implementation, the additional additive and the compound represented by Chemical Formula 1 may be included in different amounts.

When the additional additive is included within the range, battery resistance may be effectively suppressed, and a rechargeable lithium battery having much excellent cycle-life characteristics may be realized.

The non-aqueous organic solvent may serve as a medium for transmitting ions taking part in the electrochemical reaction of a battery.

The non-aqueous organic solvent may include, e.g., a carbonate solvent, an ester solvent, an ether solvent, a ketone solvent, an alcohol solvent, or an aprotic solvent.

The carbonate solvent may include, e.g., dimethyl carbonate (DMC), diethyl carbonate (DEC), dipropyl carbonate (DPC), methylpropyl carbonate (MPC), ethylpropyl carbonate (EPC), methylethyl carbonate (MEC), ethylene carbonate (EC), propylene carbonate (PC), butylene carbonate (BC), or the like. The ester solvent may include, e.g., methyl acetate, ethyl acetate, n-propyl acetate, dimethylacetate, methylpropionate, ethylpropionate, propylpropionate, decanolide, mevalonolactone, caprolactone, or the like. The ether solvent may include, e.g., dibutyl ether, tetraglyme, diglyme, dimethoxyethane, 2-methyltetrahydrofuran, tetrahydrofuran, or the like. The ketone solvent may include, e.g., cyclohexanone or the like. The alcohol solvent may include, e.g., ethanol, isopropyl alcohol, or the like. The aprotic solvent may include, e.g., nitriles such as R'—CN (wherein R' is a hydrocarbon group having a C2 to C20 linear, branched, or cyclic structure and may include a double bond, an aromatic ring, or an ether bond), and the like, dioxolanes such as 1,3-dioxolane, and the like, sulfolanes, or the like.

The non-aqueous organic solvent may be used alone or in a mixture. When the organic solvent is used in a mixture, a mixture ratio may be selected in accordance with a desirable battery performance.

In an implementation, the carbonate solvent may be prepared by mixing a cyclic carbonate and a linear carbonate. When the cyclic carbonate and linear carbonate are mixed together in a volume ratio of about 1:1 to about 1:9, electrolyte performance may be improved.

The non-aqueous organic solvent may further include an aromatic hydrocarbon organic solvent in addition to the carbonate solvent. Herein, the carbonate solvent and the aromatic hydrocarbon organic solvent may be mixed in a volume ratio of about 1:1 to about 30:1.

The aromatic hydrocarbon organic solvent may be an aromatic hydrocarbon compound of Chemical Formula 2.

[Chemical Formula 2]

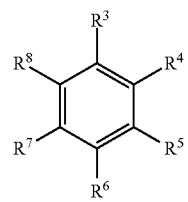

In Chemical Formula 2, $R^3$ to $R^8$ may independently include hydrogen, a halogen, a C1 to C10 alkyl group, a haloalkyl group, and a combination thereof.

Examples of the aromatic hydrocarbon organic solvent may include benzene, fluorobenzene, 1,2-difluorobenzene, 1,3-difluorobenzene, 1,4-difluorobenzene, 1,2,3-trifluorobenzene, 1,2,4-trifluorobenzene, chlorobenzene, 1,2-dichlorobenzene, 1,3-dichlorobenzene, 1,4-dichlorobenzene, 1,2,3-trichlorobenzene, 1,2,4-trichlorobenzene, iodobenzene, 1,2-diiodobenzene, 1,3-diiodobenzene, 1,4-diiodobenzene, 1,2,3-triiodobenzene, 1,2,4-triiodobenzene, toluene, fluorotoluene, 2,3-difluorotoluene, 2,4-difluorotoluene, 2,5-difluorotoluene, 2,3,4-trifluorotoluene, 2,3,5-trifluorotoluene, chlorotoluene, 2,3-dichlorotoluene, 2,4-dichlorotoluene, 2,5-dichlorotoluene, 2,3,4-trichlorotoluene, 2,3,5-trichlorotoluene, iodotoluene, 2,3-diiodotoluene, 2,4-diiodotoluene, 2,5-diiodotoluene, 2,3,4-triiodotoluene, 2,3,5-triiodotoluene, xylene, and a combination thereof.

The electrolyte may further include vinylene carbonate or an ethylene carbonate compound represented by Chemical Formula 3 in order to help improve cycle-life of a battery.

[Chemical Formula 3]

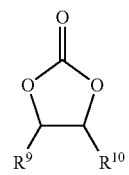

In Chemical Formula 3, $R^9$ and $R^{10}$ may independently include hydrogen, a halogen, a cyano group (CN), a nitro group (NO$_2$), and a fluorinated C1 to C5 alkyl group, provided that at least one of $R^9$ and $R^{10}$ is a halogen, a cyano group (CN), a nitro group (NO$_2$), and a fluorinated C1 to C5 alkyl group and $R^9$ and $R^{10}$ are not simultaneously hydrogen.

Examples of the ethylene carbonate compound may be difluoroethylene carbonate, chloroethylene carbonate, dichloroethylene carbonate, bromoethylene carbonate, dibromoethylene carbonate, nitroethylene carbonate, cyano-ethylene carbonate, or fluoroethylene carbonate. The amount of the additive for improving cycle-life may be used within a suitable range.

The lithium salt dissolved in the non-organic solvent supplies lithium ions in a battery, enables a basic operation of a rechargeable lithium battery, and improves transportation of the lithium ions between positive and negative electrodes. Examples of the lithium salt may include $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_2$, $LiAlCl_4$, $LiN(C_xF_{2x+1}SO_2)(C_yF_{2y+1}SO_2)$ (wherein x and y are natural numbers, e.g., an integer ranging from 1 to 20), LiCl, LiI and $LiB(C_2O_4)_2$ (lithium bis(oxalato) borate; LiBOB). The lithium salt may be used in a concentration ranging from about 0.1 M to about 2.0 M. When the lithium salt is included at the above concentration range, an electrolyte may have excellent performance and lithium ion mobility due to optimal electrolyte conductivity and viscosity.

Another embodiment provides a rechargeable lithium battery including a positive electrode; a negative electrode; and the electrolyte.

The positive electrode includes a current collector and a positive active material layer disposed on the current collector and including a positive active material.

The positive active material may include lithiated intercalation compounds that reversibly intercalate and deintercalate lithium ions.

For example, at least one composite oxide of lithium and a metal of cobalt, manganese, nickel, or a combination thereof may be used.

Examples of the positive active material may include a compound represented by one of following chemical formulae.

$Li_aA_{1-b}X_bD_2$ (0.90≤a≤1.8, 0≤b≤0.5); $Li_aA_{1-b}X_bO_{2-c}D_c$ (0.90≤a≤1.8, 0≤b≤0.5, 0≤c≤0.05); $Li_aE_{1-b}X_bO_{2-c}D_c$ (0.90≤a≤1.8, 0≤b≤0.5, 0≤c≤0.05); $Li_aE_{2-b}X_bO_{4-c}D_c$ (0.90≤a≤1.8, 0≤b≤0.5, 0≤c≤0.05); $Li_aNi_{1-b-c}Co_bX_cD_\alpha$ (0.90≤a≤1.8, 0≤b≤0.5, 0≤c≤0.5, 0≤α≤2); $Li_aNi_{1-b-c}Co_bX_cO_{2-\alpha}T_\alpha$ (0.90≤a≤1.8, 0≤b≤0.5, 0≤c≤0.05, 0≤α≤2); $Li_aNi_{1-b-c}Co_bX_cO_{2-\alpha}T_2$ (0.90≤a≤1.8, 0≤b≤0.5, 0≤c≤0.05, 0≤α<2); $Li_aNi_{1-b-c}Mn_bX_cD_\alpha$ (0.90≤a≤1.8, 0≤b≤0.5, 0≤c≤0.05, 0<α≤2); $Li_aNi_{1-b-c}Mn_bX_cO_{2-\alpha}T_\alpha$ (0.90≤a≤1.8, 0≤b≤0.5, 0≤c≤0.05, 0<α≤2); $Li_aNi_{1-b-c}Mn_bX_cO_{2-\alpha}T_2$ (0.90≤a≤1.8, 0≤b≤0.5, 0≤c≤0.05, 0<α<2); $Li_aNi_bE_cG_dO_2$ (0.90≤a≤1.8, 0≤b≤0.9, 0≤c≤0.5, 0.001≤d≤0.1); $Li_aNi_bCo_cMn_dG_eO_2$ (0.90≤a≤1.8, 0≤b≤0.9, 0≤c≤0.5, 0≤d≤0.5, 0.001≤e≤0.1); $Li_aNiG_bO_2$ (0.90≤a≤1.8, 0.001≤b≤0.1); $Li_aCoG_bO_2$ (0.90≤a≤1.8, 0.001≤b≤0.1); $Li_aMn_{1-b}G_bO_2$ (0.90≤a≤1.8, 0.001≤b≤0.1); $Li_aMn_2G_bO_4$ (0.90≤a≤1.8, 0.001≤b≤0.1); $Li_aMn_{1-g}G_gPO_4$ (0.90≤a≤1.8, 0≤g≤0.5); $QO_2$; $QS_2$; $LiQS_2$; $V_2O_5$; $LiV_2O_5$; $LiZO_2$; $LiNiVO_4$; $Li_{(3-f)}J_2(PO_4)_3$ (0≤f≤2); $Li_{(3-f)}Fe_2(PO_4)_3$ (0≤f≤2); $Li_aFePO_4$ (0.90≤a≤1.8)

In chemical formulae, A is selected from Ni, Co, Mn, and a combination thereof; X is selected from Al, Ni, Co, Mn, Cr, Fe, Mg, Sr, V, a rare earth element, and a combination thereof; D is selected from O, F, S, P, and a combination thereof; E is selected from Co, Mn, and a combination thereof; T is selected from F, S, P, and a combination thereof; G is selected from Al, Cr, Mn, Fe, Mg, La, Ce, Sr, V, and a combination thereof; Q is selected from Ti, Mo, Mn, and a combination thereof; Z is selected from Cr, V, Fe, Sc, Y, and a combination thereof; and J is selected from V, Cr, Mn, Co, Ni, Cu, and a combination thereof.

The compounds may have a coating layer on a surface thereof, or may be mixed with another compound having a coating layer. The coating layer may include at least one coating element compound, e.g., an oxide of a coating element, a hydroxide of a coating element, an oxyhydroxide of a coating element, an oxycarbonate of a coating element, and a hydroxy carbonate of a coating element. The compound for the coating layer may be amorphous or crystalline. The coating element included in the coating layer may include Mg, Al, Co, K, Na, Ca, Si, Ti, V, Sn, Ge, Ga, B, As, Zr, or a mixture thereof. The coating layer may be formed by a method having no adverse influence on properties of a positive active material by using these elements in the compound. For example, the method may include a suitable coating method (e.g., spray coating, dipping, etc.).

Examples of the positive active material according to an embodiment may include $Li_xNi_yCo_zAl_{1-y-z}O_2$ (1≤x≤1.2, 0.5≤y≤1, and 0≤z≤0.5).

The positive active material may be included in an amount of about 90 wt % to about 98 wt % based on a total weight of the positive active material layer.

In an implementation, the positive active material layer may include a binder and a conductive material. Herein, the binder and the conductive material may be included in an amount of about 1 wt % to about 5 wt %, respectively based on a total weight of the positive active material layer.

The binder plays a role of adhering positive active material particles one another and in addition, the positive active material particles to a current collector. Examples of the binder may include polyvinyl alcohol, carboxylmethyl cellulose, hydroxypropyl cellulose, diacetyl cellulose, polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, a styrene-butadiene rubber, an acrylated styrene-butadiene rubber, an epoxy resin, nylon, and the like.

The conductive material is included to provide electrode conductivity. A suitable electrically conductive material may be used as a conductive material unless it causes an adverse chemical change. Examples of the conductive material may include a carbon material such as natural graphite, artificial graphite, carbon black, acetylene black, ketjen black, a carbon fiber, and the like; a metal material of a metal powder or a metal fiber including copper, nickel, aluminum, silver, and the like; a conductive polymer such as a polyphenylene derivative; or a mixture thereof.

The current collector may include, e.g., Al.

The negative electrode includes a current collector and a negative active material layer formed on the current collector and including a negative active material.

The negative active material may include a material that reversibly intercalates/deintercalates lithium ions, a lithium metal, a lithium metal alloy, a material being capable of doping/dedoping lithium, or transition metal oxide.

The material that reversibly intercalates/deintercalates lithium ions may include a carbon material. The carbon material may be a suitable carbon negative active material in a rechargeable lithium ion battery. Examples thereof may include crystalline carbon, amorphous carbon, or a mixture thereof. The crystalline carbon may be non-shaped, or sheet, flake, spherical, or fiber shaped natural graphite or artificial graphite. The amorphous carbon may be a soft carbon, a hard carbon, a mesophase pitch carbonization product, fired coke, and the like.

The lithium metal alloy includes an alloy of lithium and a metal selected from Na, K, Rb, Cs, Fr, Be, Mg, Ca, Sr, Si, Sb, Pb, In, Zn, Ba, Ra, Ge, Al, and Sn.

The material being capable of doping/dedoping lithium may be Si, Si—C composite, $SiO_x$ (0<x<2), a Si-Q alloy (wherein Q is an element selected from an alkali metal, an alkaline-earth metal, a Group 13 element, a Group 14 element, a Group 15 element, a Group 16 element, a transition metal, a rare earth element, and a combination thereof, and not Si), Sn, $SnO_2$, a Sn—R alloy (wherein R is an element selected from an alkali metal, an alkaline-earth metal, a Group 13 element, a Group 14 element, a Group 15 element, a Group 16 element, a transition metal, a rare earth element, and a combination thereof, and not Sn), and the like. At least one of these materials may be mixed with $SiO_2$. The elements Q and R may be selected from Mg, Ca, Sr, Ba, Ra, Sc, Y, Ti, Zr, Hf, Rf, V, Nb, Ta, Db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Tl, Ge, P, As, Sb, Bi, S, Se, Te, Po, and a combination thereof.

The transition metal oxide may be vanadium oxide, lithium vanadium oxide, or lithium titanium oxide.

In the negative active material layer, the negative active material may be included in an amount of about 95 wt % to about 99 wt % based on the total weight of the negative active material layer.

In an implementation, the negative active material layer includes a binder, and optionally a conductive material. In the negative active material layer, a content of the binder may be about 1 wt % to about 5 wt % based on a total weight of the negative active material layer. When the negative active material layer includes a conductive material, the negative active material layer may include about 90 wt % to about 98 wt % of the negative active material, about 1 wt % to about 5 wt % of the binder, and about 1 wt % to about 5 wt % of the conductive material.

The binder improves binding properties of negative active material particles with one another and with a current collector. The binder may include a non-water-soluble binder, a water-soluble binder, or a combination thereof.

The non-water-soluble binder may include polyvinylchloride, carboxylated polyvinylchloride, polyvinylfluoride, an ethylene oxide-containing polymer, polyvinylpyrrolidone, polyurethane, polytetrafluoroethylene, polyvinylidene fluoride, polyethylene, polypropylene, polyamideimide, polyimide, or a combination thereof.

The water-soluble binder may be a rubber binder or a polymer resin binder. The rubber binder may include a styrene-butadiene rubber, an acrylated styrene-butadiene rubber (SBR), an acrylonitrile-butadiene rubber, an acrylic rubber, a butyl rubber, a fluorine rubber, or a combination thereof. The polymer resin binder may include polytetrafluoroethylene, polyethylene, polypropylene, ethylenepropylenecopolymer, polyethyleneoxide, polyvinylpyrrolidone, polyepichlorohydrine, polyphosphazene, polyacrylonitrile, polystyrene, an ethylenepropylenediene copolymer, polyvinylpyridine, chlorosulfonated polyethylene, latex, a polyester resin, an acrylic resin, a phenolic resin, an epoxy resin, polyvinyl alcohol, or a combination thereof.

When the water-soluble binder is used as a negative electrode binder, a cellulose compound may be further used to provide viscosity as a thickener. The cellulose compound may include carboxymethyl cellulose, hydroxypropylmethyl cellulose, methyl cellulose, or alkali metal salts thereof. The alkali metals may be Na, K, or Li. Such a thickener may be included in an amount of about 0.1 to about 3 parts by weight based on 100 parts by weight of the negative active material.

The conductive material is included to provide electrode conductivity. A suitable electrically conductive material may be used as a conductive material unless it causes an adverse chemical change. Examples of the conductive material include a carbon material such as natural graphite, artificial graphite, carbon black, acetylene black, ketjen black, a carbon fiber, and the like; a metal material of a metal powder or a metal fiber including copper, nickel, aluminum silver, and the like; a conductive polymer such as a polyphenylene derivative; or a mixture thereof.

The current collector may include a copper foil, a nickel foil, a stainless steel foil, a titanium foil, a nickel foam, a copper foam, a polymer substrate coated with a conductive metal, or a combination thereof.

The rechargeable lithium battery may further include a separator between the negative electrode and the positive electrode, depending on a type of the rechargeable lithium battery. Examples of a suitable separator material may include polyethylene, polypropylene, polyvinylidene fluoride, and multi-layers thereof such as a polyethylene/polypropylene double-layered separator, a polyethylene/polypropylene/polyethylene triple-layered separator, and a polypropylene/polyethylene/polypropylene triple-layered separator.

Referring to FIG. 1, a rechargeable lithium battery 100 according to an embodiment may include a battery cell including a negative electrode 112, a positive electrode 114 facing the negative electrode 112, a separator 113 between the negative electrode 112 and the positive electrode 114, and an electrolyte for a rechargeable lithium battery impregnating the negative electrode 112, the positive electrode 114, and the separator 113, a battery case 120 housing the battery cell, and a sealing member 140 sealing the battery case 120.

Hereinafter, examples of the present disclosure and comparative examples are described. These examples, however, are not in any sense to be interpreted as limiting the scope of the invention.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Manufacture of Rechargeable Lithium Battery Cell

Preparation Example 1: Synthesis of 2-[(methylsulfonyl)methyl]-oxirane

2-[(methylsulfonyl)methyl]-oxirane was synthesized as follows.

9 g of allyl methyl sulfide dissolved in 150 mL of methanol was added to 200 mL of hydrogen peroxide (a 30% aqueous solution) and then, mixed with 2.5 g of ammonium molybdate.

The mixture was stirred at ambient temperature for 1.5 hours and then, extracted with saturated brine and 1,2-dichloromethane to obtain 10 g of allylmethyl sulfone. 300 mL of 1,2-dichloromethane including the crude product was refluxed with 28 g of m-chloroperoxy benzoic acid for 20 hours. The reaction product was cooled down to ambient temperature, and a filtrate was dried under vacuum after filtering a white precipitate to obtain a crude product, and subsequently, silica gel column chromatography (ethyl acetate/hexane (v/v)=1/4 to 1/1) was performed to obtain 2-[(methylsulfonyl)methyl]-oxirane represented by Chemical Formula 1a as light white oil (6.78 g, 48%).

[Chemical Formula 1a]

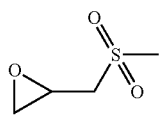

1H NMR (400 MHz, CDCl3) 2.68-2.70 (dd, 1H), 2.92-3.00 (m, 2H), 3.02 (s, 3H), 3.38-3.45 (m, 2H)

Preparation Example 2: Synthesis of Methyl-2,3-epoxypropanesulfonate

A solution obtained by dissolving methyl allylsulfonate (10 g) and m-chloro peroxybenzoic acid in dichloromethane was stirred at ambient temperature for several days (4 to 5 days). The reaction mixture was evaporated until the volume was reduced to a half, and a white precipitate was filtered. A filtrate therefrom was dried under vacuum to obtain a crude product and subsequently, treated through column chromatography with silica gel (ethyl acetate/hexane (v/v) =1/4 to 1/1) to obtain methyl-2,3-epoxypropanesulfonate represented by Chemical Formula 1b as a light white oil (5 g, 45%).

1H NMR (400 MHz, CDCl3) 2.69-2.71 (dd, 1H), 2.95 (t, 1H), 3.31-3.40 (m, 3H), 3.97 (s, 3H)

[Chemical Formula 1b]

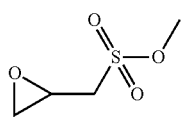

The methyl allylsulfonate of Preparation Example 2 was prepared in a synthesis method as follows.

A pyridine (19.7 g) methanol solution (35 mL) was added in a dropwise fashion to an allyl sulfonyl chloride (35 g) methanol solution (70 mL) cooled down to 0° C. After stirring for 30 minutes, the reaction product was refluxed for 6 hours. When the reaction was complete, a solvent was evaporated therefrom to obtain a dried crude product, pyridinium allylsulfonate salt. The crude product was suspended in 45 g of cyclohexane (250 mL) by adding dimethylsulfate (42.5 g) thereto, and the reaction product was refluxed for 24 hours. A solvent was evaporated and distilled therefrom to obtain methyl allylsulfonate with a yield of 73%.

Preparation Example 3: Synthesis of 2-(methylsulfonyl)-oxirane 2-(methylsulfonyl)-oxirane was synthesized in a method as follows.

n-butyllithium (22.0 mmol, 14 mL of a 1.6 M solution in hexanes, 1.0 equiv.) was added to a solution of tert-butyl hydroperoxide (33 mmol, 6 mL of an about 5 M solution in decane, 1.5 equiv.) dissolved in THF (300 mL) at −78° C. under a nitrogen atmosphere. The mixed solution was stirred for 15 minutes and warmed up to −15° C. Subsequently, a solution of methyl vinyl sulfone (2.34 g. 22.0 mmol, 1 equiv.) dissolved in distilled THF (50 mL) was added thereto and then, stirred at −15° C. for 2.5 h. A saturated sodium sulfite aqueous solution was added thereto, and the obtained mixed solution was extracted with ethyl acetate. An extract therefrom was dried with sodium sulfate, filtered, dried under vacuum, and treated through column chromatography (PE/EtOAc) to obtain 2-(methylsulfonyl)-oxirane represented by Chemical Formula 1c in an oil state having viscosity (0.7 g, 26%).

[Chemical Formula 1c]

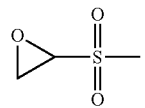

Example 1

A positive active material slurry was prepared by using $LiNi_{0.8}Co_{0.15}Al_{0.05}O_2$ as a positive active material, polyvinylidene fluoride as a binder, and ketjen black as a conductive material in a weight ratio of 97.3:1.4:1.3 and dispersing the mixture in N-methyl pyrrolidone.

The positive active material slurry was coated on a 15 μm-thick Al foil, dried at 100° C., and pressed to manufacture a positive electrode.

A negative active material slurry was prepared by mixing graphite as a negative active material, polyvinylidene fluoride as a binder, and ketjen black as a conductive material in a weight ratio of 98:1:1 and then, dispersing the mixture in N-methyl pyrrolidone.

The negative active material slurry was coated on a 10 μm-thick Cu foil, dried at 100° C., and compressed to manufacture a negative electrode.

The positive and negative electrodes, a 25 μm-thick polyethylene separator, and an electrolyte were used to manufacture a rechargeable lithium battery cell.

The electrolyte had the following composition.

(Electrolyte Composition)

Salt: $LiPF_6$ 1.5 M

Solvent: ethylene carbonate:fluoroethylene carbonate:dimethyl carbonate (EC:FEC:DMC=volume ratio of 2:2:6)

Additive: 1 wt % of 2-[(methylsulfonyl)methyl]-oxirane represented by Chemical Formula 1a, 0.2 wt % of $LiBF_4$, 1 wt % of SN, 1 wt % of LiBOB, and 1.5 wt % of $LiPO_2F_2$

[Chemical Formula 1a]

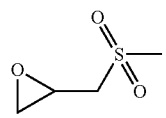

(Herein, in the electrolyte composition, "wt %" is based on a total weight of the electrolyte (a lithium salt+a non-aqueous organic solvent+an additive))

Example 2

A rechargeable lithium battery cell was manufactured according to the same method as Example 1 except that methyl-2,3-epoxypropanesulfonate represented by Chemical Formula 1b in an amount of 1 wt % was used instead of the 2-[(methylsulfonyl)methyl]-oxirane in the additive composition.

[Chemical Formula 1b]

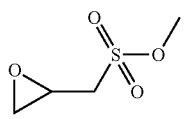

Comparative Example 1

A rechargeable lithium battery cell was manufactured according to the same method as Example 1 except that the 2-[(methylsulfonyl)methyl]-oxirane was not included.

Comparative Example 2

A rechargeable lithium battery cell was manufactured according to the same method as Example 1 except that 2-(methylsulfonyl)-oxirane represented by Chemical Formula 1c in an amount of 1 wt % was used instead of the 2-[(methylsulfonyl)methyl]-oxirane in the electrolyte composition.

[Chemical Formula 1c]

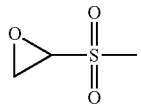

Battery Characteristics Evaluation

Evaluation 1: CV Characteristics

Figure 2:
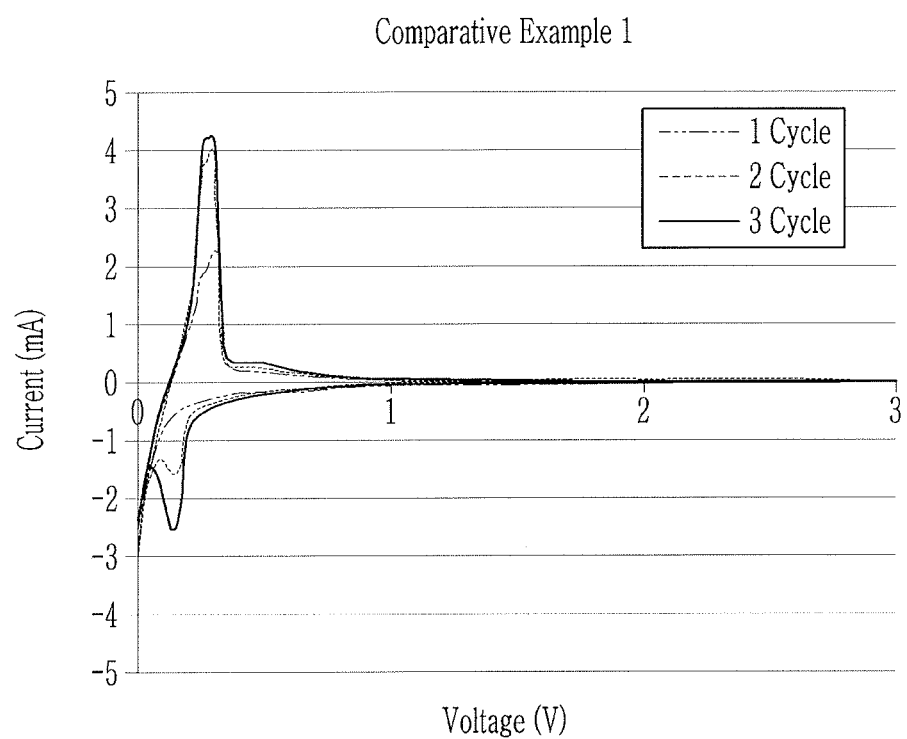
FIG. 2 illustrates a graph showing a negative electrode cyclic voltammetry (CV) of the electrolyte according to Comparative Example 1.
Figure 3:
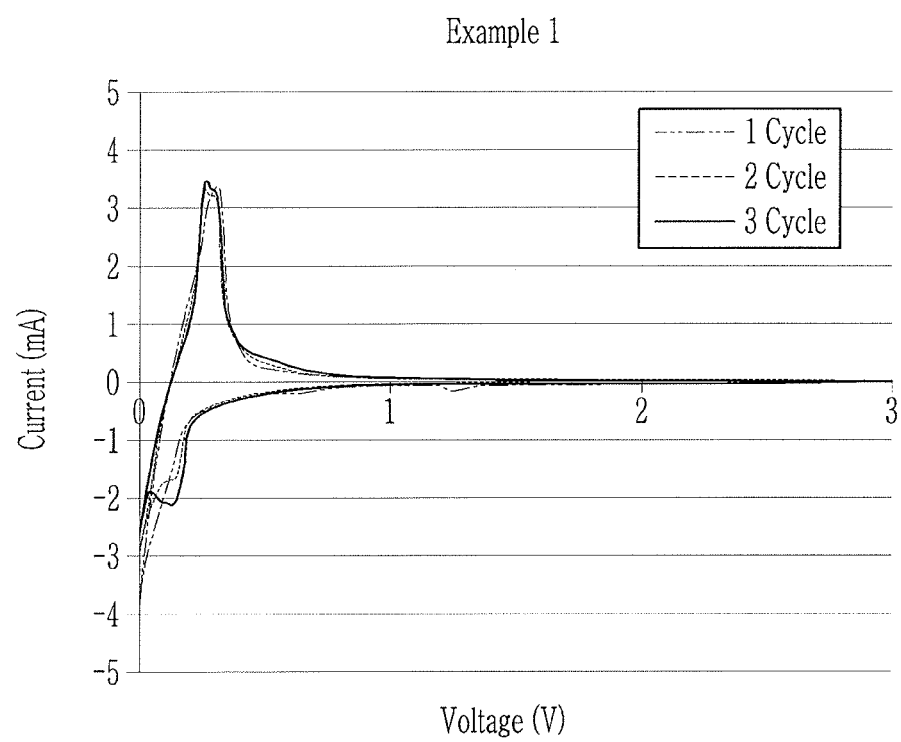
FIG. 3 illustrates a graph showing a negative electrode cyclic voltammetry (CV) of the electrolyte according to Example 1.
Figure 4:
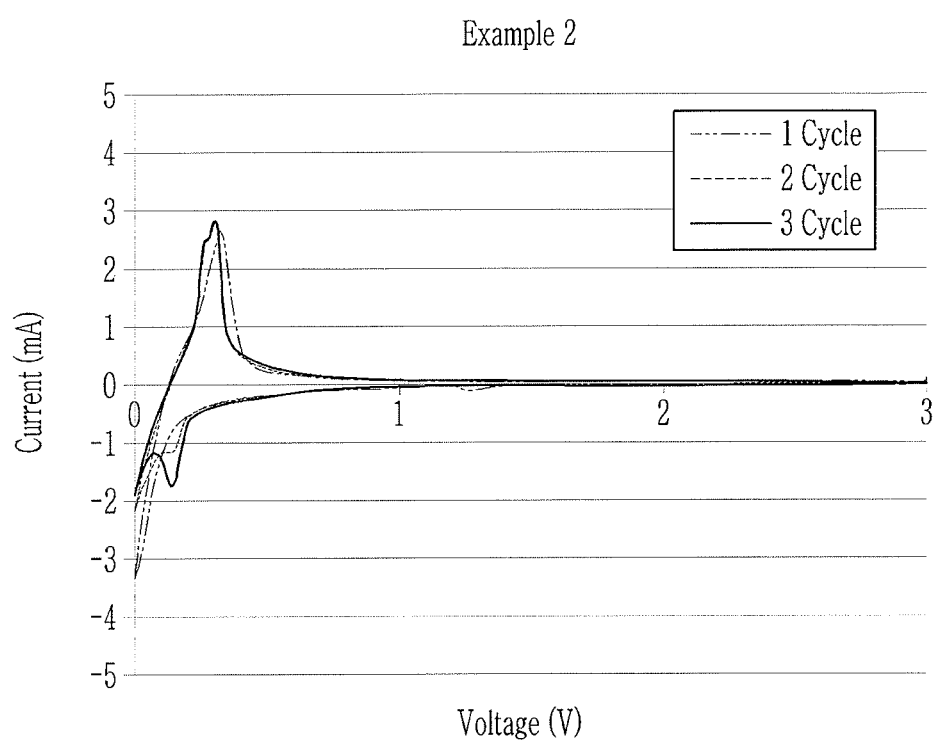
FIG. 4 illustrates a graph showing a negative electrode cyclic voltammetry (CV) of the electrolyte according to Example 2.

Electrochemical stability of the rechargeable lithium battery cells according to Comparative Example 1, Example 1, and Example 2 was evaluated by measuring cyclic voltammetry (CV), and the results are shown in FIGS. 2 to 4.

A negative electrode cyclic voltammetry (CV) was measured by using a triple electrode electrochemical cell using graphite as a working electrode and Li metals as a reference electrode and a counter electrode. Herein, scan was 3 cycles performed from 3 V to 0 V and from 0 V to 3 V at a rate of 0.1 mV/sec.

FIG. 2 illustrates a graph showing a negative electrode cyclic voltammetry (CV) of the electrolyte according to Comparative Example 1.

FIG. 3 illustrates a graph showing a negative electrode cyclic voltammetry (CV) of the electrolyte according to Example 1.

FIG. 4 illustrates a graph showing a negative electrode cyclic voltammetry (CV) of the electrolyte according to Example 2.

As shown in FIGS. 3 and 4, in the cyclic voltammetry curves of three-electrode cells respectively including the electrolytes according to Examples 1 and 2, a reduction peak appeared according to one cycle, but as shown in FIG. 2, in a cyclic voltammetry curve of a three-electrode cell including the electrolyte according to Comparative Example 1, a reduction peak did not appear at all. Referring to the results, in the rechargeable lithium battery cells respectively including the electrolytes according to Examples 1 and 2, an initial SEI film may be expected to be formed in a negative electrode over a wide voltage region before a solvent was decomposed during the charge that lithium ions were inserted into the negative electrode. Accordingly, the rechargeable lithium battery cell according to Example 1 would exhibit excellent battery performance compared with the rechargeable lithium battery having no initial SEI film according to Comparative Example 1.

Evaluation 2: Cycle-Life Characteristics

Figure 5:
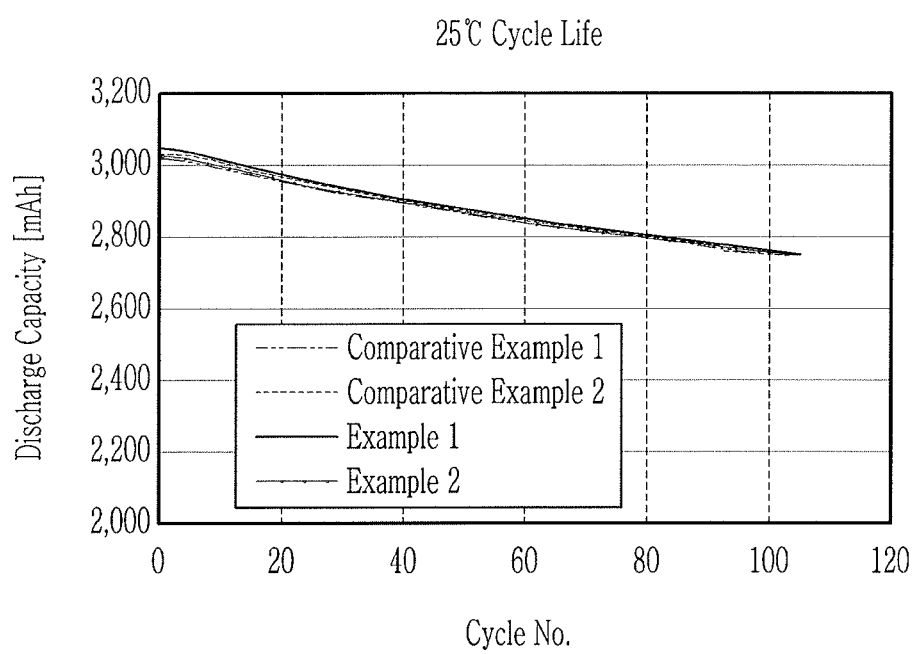
FIG. 5 illustrates a graph showing discharge capacity according to cycles of rechargeable lithium battery cells according to Example 1 and 2 and Comparative Examples 1 and 2.

The rechargeable lithium battery cells according to Examples 1 and 2 and Comparative Examples 1 and 2 were charged at CC-CV of 4 A and 4.2 V and a cut-off of 100 mA and discharged at CC of 10 A and a cut-off of 2.5 V as one cycle at ambient temperature, the charge and discharge was 100 cycles repeated to evaluate cycle-life characteristics of the cells, and the results are shown in FIG. 5, and capacity retentions after the 100 cycles are shown in Table 1.

FIG. 5 illustrates a graph showing discharge capacity according to cycles of rechargeable lithium battery cells according to Example 1 and 2 and Comparative Examples 1 and 2.

Referring to FIG. 5 and Table 1, Examples 1 and 2 exhibited excellent charge and discharge cycle characteristics compared with Comparative Examples 1 and 2, and accordingly, a rechargeable lithium battery cell including a compound represented by Chemical Formula 1 as an additive shows excellent cycle-life characteristics.

TABLE 1

| | Initial discharge capacity (mAh) | Discharge capacity after 100 cycles (mAh) | Capacity retention (%) after 100 cycles |
|---|---|---|---|
| Comparative Example 1 | 3008 | 2751 | 91 |
| Comparative Example 2 | 3023 | 2751 | 91 |
| Example 1 | 3029 | 2785 | 92 |
| Example 2 | 3012 | 2771 | 92 |

Evaluation 3: Impedance (Resistance Increase Rate) Placed at High Temperature

Figure 6:
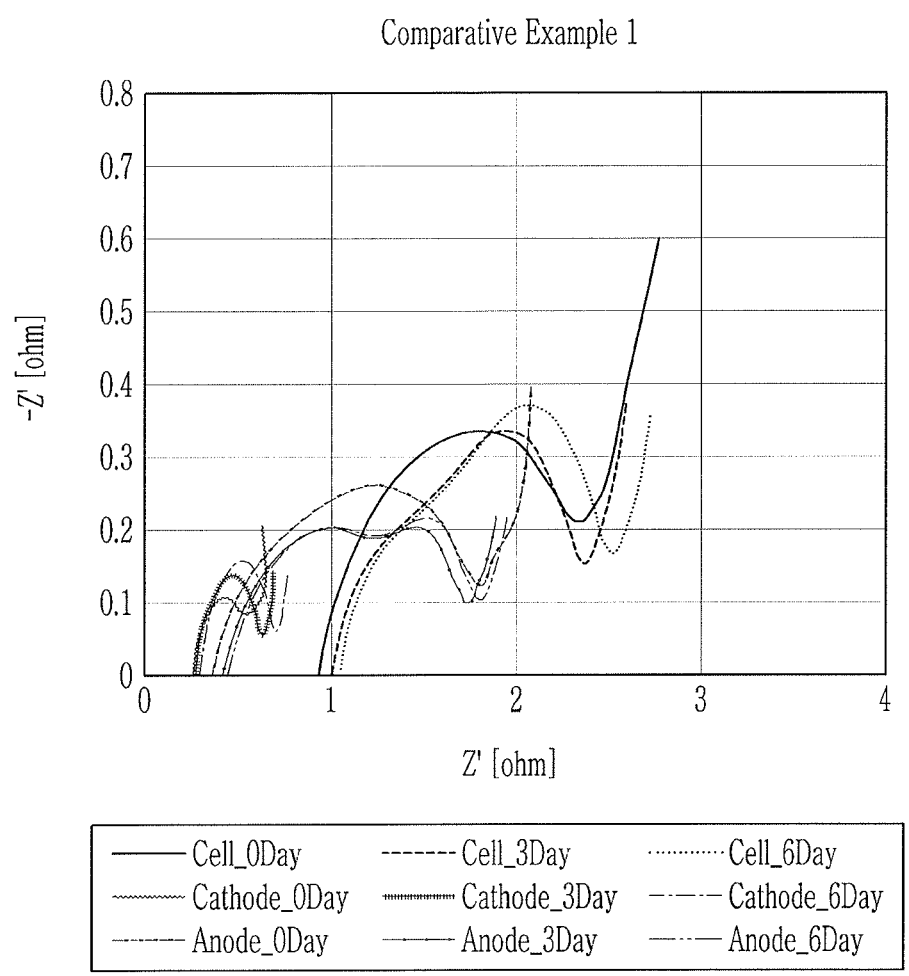
FIG. 6 illustrates a Nyquist plot showing the result of impedance analysis after placing the rechargeable lithium battery cell according to Comparative Example 1 at a high temperature.
Figure 7:
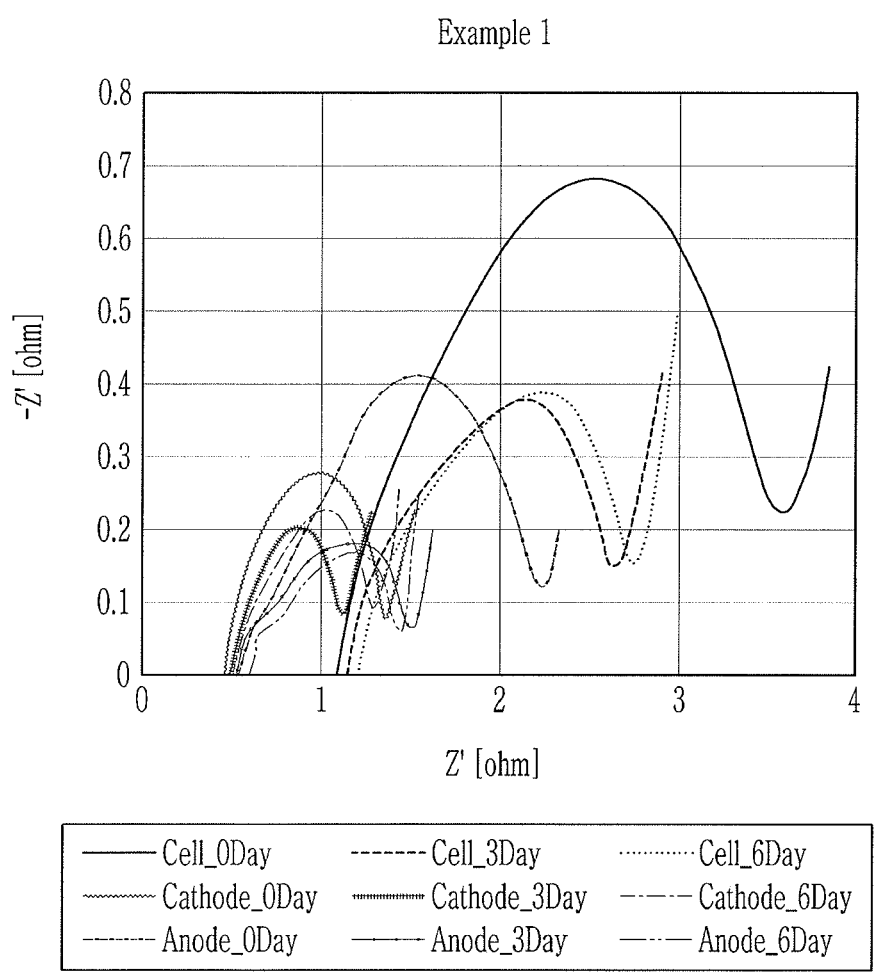
FIG. 7 illustrates a Nyquist plot showing the result of impedance analysis after placing the rechargeable lithium battery cell according to Example 1 at a high temperature.
Figure 8:
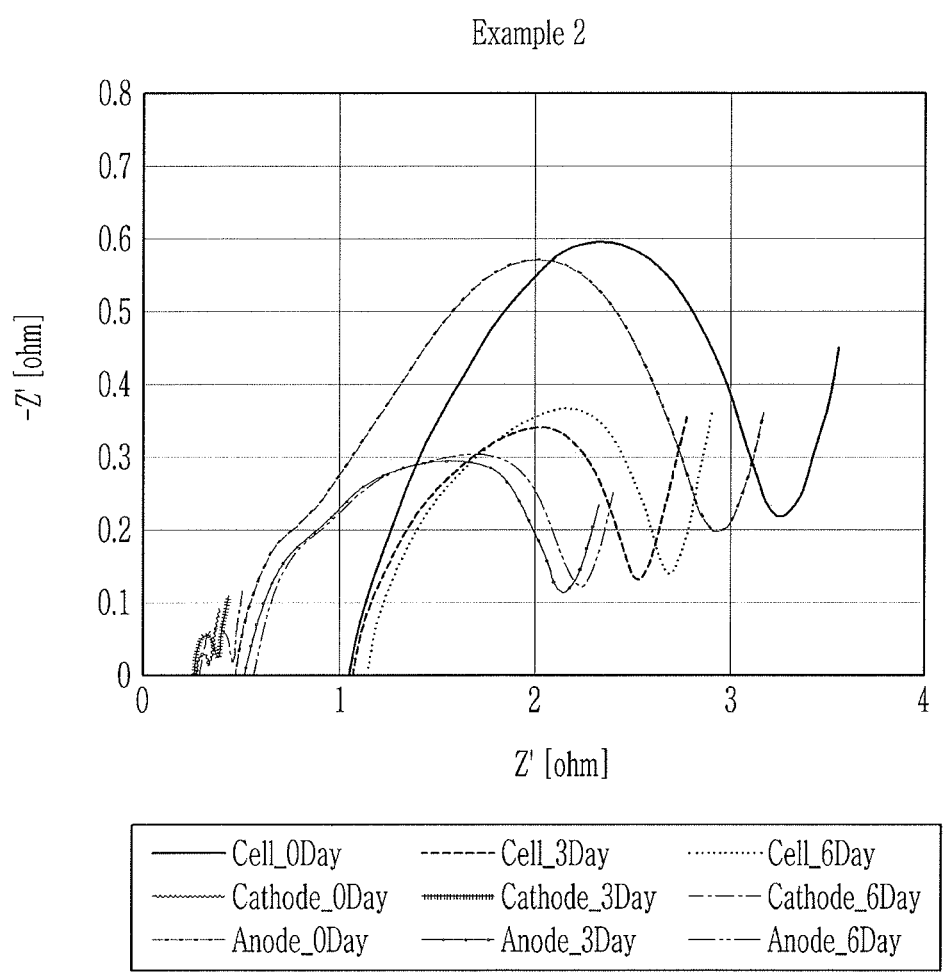
FIG. 8 illustrates a Nyquist plot showing the result of impedance analysis after placing the rechargeable lithium battery cell according to Example 2 at a high temperature.

Impedances of the rechargeable lithium battery cells according to Examples 1 and 2 and Comparative Example 1 before and after being placed at a high temperature of 60° C. were measured, and the results are shown in FIGS. 6 to 8.

The impedances were measured by using VMP3B-10 made by BioLogic Science Instruments Pvt Ltd.

FIG. 6 illustrates a Nyquist plot showing the result of impedance analysis after placing the rechargeable lithium battery cell according to Comparative Example 1 at a high temperature.

FIG. 7 illustrates a Nyquist plot showing the result of impedance analysis after placing the rechargeable lithium battery cell according to Example 1 at a high temperature.

FIG. 8 illustrates a Nyquist plot showing the result of impedance analysis after placing the rechargeable lithium battery cell according to Example 2 at a high temperature.

Referring to FIGS. 6 to 8, the rechargeable lithium battery cells according to Examples 1 and 2 showed low impedance compared with the rechargeable lithium battery cell according to Comparative Example 1 after being placed at a high temperature.

For example, the rechargeable lithium battery cell according to Comparative Example 1 showed an initial resistance increase of a negative electrode, but the rechargeable lithium battery cells according to Examples 1 and 2 showed no initial resistance increase, and the reason that the rechargeable lithium battery cells according to Examples 1 and 2 showed low resistance increase may be because the resistance was stably maintained due to formation of the initial SEI film on the negative electrode as a cycle-life proceeded.

In addition, a protective layer tended to be formed on a positive electrode as for Example 1.

Evaluation 4: Storage Characteristics at High Temperature

Each rechargeable lithium battery according to Examples 1 and 2 and Comparative Examples 1 and 2 was placed for 30 days at 60° C. in a charge state (SOC, a state of charge=100%), and impedance (a resistance increase rate) thereof when stored at a high temperature of 60° C. was evaluated. The results are shown in Table 2.

An initial formation condition was to discharge down to 2.6 V after CC charge up to 3.6 V at a current of 0.2 C at the first cycle and then, to discharge down to 2.6 V after charge up to 4.2 V at a current of 0.2 C at the second cycle, and accordingly, an oxide film was formed on the surface of an electrode.

Initial capacity and capacity after being placed for 30 days were obtained by measuring discharge capacity after performing a CC-CV charge up to 4.2 V at a current of 1 C and then, a cut-off to 2.6 V at a current of 3 C.

A capacity retention (%) was obtained as a percentage of the capacity after being stored for 30 days relative to the initial capacity.

DC resistance (DC-IR) was measured as follows.

The DC resistance (DC-IR) was calculated from each current difference and voltage difference when different currents were applied.

In a full charge state, a constant current discharge of 10 A was performed for 10 seconds.

Next, after the constant current discharge of 10 A for 10 seconds, a constant current discharge of 10 A was performed for 4 seconds.

The DC resistance (DC-IR) was calculated according to a formula of $\Delta R=\Delta V/\Delta I$ from data of 18 seconds and 23 seconds.

Impedance (%) was obtained as a percentage of DC-IR after being stored for 30 days relative to initial DC-IR.

TABLE 2

|  | Initial | 60° C. @ 30 days | |
| --- | --- | --- | --- |
|  | DC-IR (mOhm) | DC-IR (mOhm) | ΔDC-IR (%) |
| Comparative Example 1 | 20.12 | 30.26 | 50.40 |
| Comparative Example 2 | 20.39 | 29.64 | 62.20 |
| Example 1 | 20.78 | 28.92 | 39.37 |
| Example 2 | 20.59 | 26.46 | 28.46 |

Referring to Table 2, Examples 1 and 2 (including an additive represented by Formula 1) exhibited low impedance, compared with Comparative Examples 1 and 2, when stored at a high temperature of 60° C. Accordingly, when a compound represented by Chemical Formula 1 was used as an additive, high temperature antioxidation and antiresistance of a battery cell in a charge state battery were improved.

Evaluation 5: High Temperature Safety

High temperature safety of the rechargeable lithium battery cells according to Examples 1 and 2 as well as Comparative Examples 1 and 2 was evaluated by measuring their CID (Current Interrupt Device) operation-starting points, and the results are shown in Table 3.

First, after twice performing a formation charge/discharge at 0.2 C/0.5 C and respectively once performing a charge/discharge experiment at standard charge/discharge current density of 0.5 C/0.2 C, a charge cut-off voltage of 4.2 V (Li/graphite), and a discharge cut-off voltage of 2.6 V (Li/graphite), the cells were placed in a 90° C. chamber for 60 hours, and CID (Current Interrupt Device) operation-starting points thereof were measured.

TABLE 3

|  | CID OPEN TIME (hr) (@ 90° C.) |
| --- | --- |
| Comparative Example 1 | 13.1 |
| Comparative Example 2 | 12 |
| Example 1 | 17 |
| Example 2 | 18.3 |

Referring to Table 3, Examples 1 and 2 including the compound represented by Chemical Formula 1 as an additive showed delayed CID open time compared with Comparative Examples 1 and 2. For example, a rechargeable lithium battery cell according to the present disclosure showed an excellent effect of suppressing gas generation when placed at a high temperature.

By way of summation and review, $LiPF_6$ may be used as a lithium salt of an electrolyte, and may react with an electrolytic solvent to promote depletion of a solvent and generate a large amount of gas. When $LiPF_6$ is decomposed, it generates LiF and $PF_5$, which leads to electrolyte depletion in the battery, resulting in degradation in high temperature performance and poor safety.

One or more embodiments may provide an electrolyte that helps suppress side reactions of such a lithium salt and helps improve the performance of the battery.

One or more embodiments may provide an electrolyte for a rechargeable lithium battery capable of ensuring high-temperature stability and thus improving battery performance.

One or more embodiments may provide a rechargeable lithium battery that may realize improved high-temperature stability and cycle-life characteristics.

DESCRIPTION OF SYMBOLS

100: rechargeable lithium battery
112: negative electrode
113: separator
114: positive electrode
120: battery case
140: sealing member Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An electrolyte for a rechargeable lithium battery, the electrolyte comprising:
   a non-aqueous organic solvent;
   a lithium salt; and
   an additive,
   wherein the additive includes a compound represented by Chemical Formula 1:

[Chemical Formula 1]

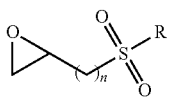

wherein, in Chemical Formula 1,
R is a substituted or unsubstituted C1 to C10 alkyl group, an unsubstituted C1 to C10 alkoxy group, a substituted or unsubstituted C2 to C10 alkenyl group, a substituted or unsubstituted C2 to C10 alkynyl group, a substituted or unsubstituted C3 to C10 cycloalkyl group, a substituted or unsubstituted C3 to C10 cycloalkenyl group, or a substituted or unsubstituted C6 to C20 aryl group, and n is an integer of 1 to 3.

2. The electrolyte for a rechargeable lithium battery as claimed in claim 1, wherein R is a substituted or unsubstituted C1 to C5 alkyl group or an unsubstituted C1 to C5 alkoxy group.

3. The electrolyte for a rechargeable lithium battery as claimed in claim 1, wherein the compound represented by Chemical Formula 1 is included in an amount of 0.1 wt % to 3 wt %, based on a total weight of the electrolyte for a rechargeable lithium battery.

4. The electrolyte for a rechargeable lithium battery as claimed in claim 1, further comprising an additional additive, the additional additive including vinylethylene carbonate, fluoroethylene carbonate, propenesultone, propanesultone, lithiumtetrafluoroborate, lithium bis(oxalato)borate, succinonitrile, lithium difluorophosphate, or 2-fluoro biphenyl.

5. The electrolyte for a rechargeable lithium battery as claimed in claim 4, wherein the additional additive is included in an amount of 0.1 wt % to 10 wt %, based on a total weight of the electrolyte for a rechargeable lithium battery.

6. The electrolyte for a rechargeable lithium battery as claimed in claim 4, wherein the additional additive and the compound represented by Chemical Formula 1 are included in a weight ratio of 5:1 to 1:5.

7. A rechargeable lithium battery, comprising:
a positive electrode;
a negative electrode; and
the electrolyte as claimed in claim 1.

8. The rechargeable lithium battery as claimed in claim 7, wherein R is a substituted or unsubstituted C1 to C5 alkyl group or an unsubstituted C1 to C5 alkoxy group.

9. The rechargeable lithium battery as claimed in claim 7, wherein the compound represented by Chemical Formula 1 is included in an amount of 0.1 wt % to 3 wt %, based on a total weight of the electrolyte for a rechargeable lithium battery.

10. The rechargeable lithium battery as claimed in claim 7, wherein the electrolyte further includes an additional additive, the additional additive including vinylethylene carbonate, fluoroethylene carbonate, propenesultone, propanesultone, lithiumtetrafluoroborate, lithium bis(oxalato)borate, succinonitrile, lithium difluorophosphate, or 2-fluoro biphenyl.

11. The rechargeable lithium battery as claimed in claim 10, wherein the additional additive is included in an amount of 0.1 wt % to 10 wt %, based on a total weight of the electrolyte for a rechargeable lithium battery.

12. The rechargeable lithium battery as claimed in claim 10, wherein the additional additive and the compound represented by Chemical Formula 1 are included in a weight ratio of 5:1 to 1:5.

* * * * *